(12) United States Patent
Ahn et al.

(10) Patent No.: US 6,855,348 B2
(45) Date of Patent: Feb. 15, 2005

(54) INSECTICIDAL COMPOSITION DERIVED FROM PLANTS

(76) Inventors: Young-Joon Ahn, 15-1108, Changril Apt., 7 Shinchoon-dong, Songpo-gu, Seoul (KR), 139-240; Young-Soo Kim, 7F, Yuhenyenghaeng Bldg., 40-6 Daabang-dong, Dongjak-gu, Seoul (KR), 156-754; Soon-Il Kim, 3F, 600-9 Guoon-dong, Kwansoon-gu, Suwon-shi, Kyonggi-do (KR), 441-340; Hyun-Kyung Kim, 112-702 Woosung Apt., Cheongilm-dong, Seo-gu, Taejon (KR)

( * ) Notice: Subject to any disclaimer, the term of this patent is extended or adjusted under 35 U.S.C. 154(b) by 0 days.

(21) Appl. No.: 09/942,107

(22) Filed: Aug. 28, 2001

(65) Prior Publication Data

US 2003/0157139 A1 Aug. 21, 2003

Related U.S. Application Data

(63) Continuation-in-part of application No. 09/776,566, filed on Feb. 2, 2001, now abandoned.

(30) Foreign Application Priority Data

Dec. 23, 2000 (KR) .......................................... 2000-81256

(51) Int. Cl.$^7$ ................................................. A01N 65/00
(52) U.S. Cl. ........................ 424/739; 424/725; 424/405; 424/755; 424/775
(58) Field of Search ................................ 424/739, 725, 424/405, 755, 775

(56) References Cited

U.S. PATENT DOCUMENTS 6,436,150 B2 * 8/2002 Watanabe et al.

FOREIGN PATENT DOCUMENTS

| CN | 1243742 A | * | 2/2000 |
| CN | 0254695 A | * | 5/2000 |
| JP | 75003367 B | * | 2/1975 |
| JP | 62019505 A | * | 1/1987 |
| JP | 01332505 A | * | 5/1989 |
| JP | 03123714 A | * | 5/1991 |
| JP | 10251108 A | * | 9/1998 |
| RU | 2099946 C1 | * | 12/1997 |

OTHER PUBLICATIONS

Ishii, R et al., Agric. Biol. Chem. (1984), 48(10): 2587–2591. Specificities of bio–antimutagens in plant kingdom.*
Jiang, Z et al., Journal of Essential Oil Research (7–8/1999), 11(4): 503–506. Composition of essential oil of *Brassica juncea* (L.) Coss. from China.*
Dinan, L. et al., Pesticide Science (1999), 55(3): 331–335. Plant natural products as insect steroid receptor agonists and antagonists.*
Kiuchi et al., Japanese Journal of Pharmacognosy (1989), 43(4): 353–359. Screening of crude drugs used in turkey for nematocidal activiry on the larva of *Toxocara canis*.*
Suzuki, J et al., Annual Report of Tokyo Metropolitan Research Laboratory of Public Health (1994), 45: 35–41. Effects of Chinese medicine for helminth (VII) minimum lethal concentration on 3rd stage larvae of *Anisakis simplex* with the natural compounds.*
Lawless, J. The Illustrated Encyclopeida of Essential Oils: The Complete Guide to the Use of Oils in Aromatherapy and Herbalism, (1995). Element Books, Boston, Ma, pp 88, 98, 112 and 113.*
Park, I et al., J. Agric. Food Chem. (May 23, 2000), 48(6): 2528–2531. Insecticidal and fumigant activities of *Cinnamomum cassia* bark–derived materials against *Mechoris ursulus* (Coleoptera: Attelabidae).*

* cited by examiner

*Primary Examiner*—Christopher R. Tate
*Assistant Examiner*—Michele C. Flood (57) ABSTRACT

An insecticide composition is isolated from *Paeonia suffruticosa, Cnidium officinale, Cinnamomum cassia,* mustard (*Brassica juncea*) and horseradish (*Cholearia aroracia*) by using methanol or by elution with a solvent including hexane and ethyl acetate. The composition can be used to eradicate house dust mites and insects found in stored products.

12 Claims, 4 Drawing Sheets

Compound III

INSECTICIDAL COMPOSITION DERIVED FROM PLANTS

This application is a continuation-in-part application Ser. No. 09/776,566, filed Feb. 2, 2001, now abandoned which application is hereby incorporated by reference in its entirety.

BACKGROUND OF THE INVENTION (a) Field of the Invention

The present invention relates to an an insecticidal composition isolated from plants, and more particularly, to crude extracts and chemical compounds from plants having insecticidal activity against mites or stored-product insects.

(b) Description of the Related Art

Mites are a significant cause of allergies, and in particular they cause bronchial asthma and nasal inflammation. Mites belonging to the Pyroglyphidae family inhabit dust. *Dermatophagoides pteronyssinus, D. farinae, D. microceras,* and *Euroglyphus maynei* cause atrophic symptoms such as bronchial asthma, nasal inflammation and eczema.

House dust mites have been found in carpets, clothes, furniture, mattress and bedclothes. House dust mites are distributed not only in temperate regions but in nearly all places of residence.

It has been reported that lindane, pirimiphos-methyl, benzyl benzoate, dibutyl phthalate and diethyl m-toluamid have an acaricidal effect (Hellet-Haupt A. and J. R. Busvine. 1974. Tests of acaricides against house dust mites (*Dermatophagoides pteronyssinus, Dermatophagoides farinae*). J. Med. Entomol. 2(5):551–558). Lindane is the most acaricidally effective and long-lasting, but due to toxicity its use has been restricted for homes. The second best acaricidal compound among the above compounds, pirimiphos-methyl, has low toxicity against mammals, and it has been put to a practical use in order to control mites inhabiting storage grain. It was reported that pirimiphos-methyl was able to control 60% of mites inhabiting carpets, and 50% of mites inhabiting chairs (Mitchell, E. B., S. Wilkins, J. McCallum Deighton and T. A. E. Platts-Mills. 1985. Reduction of house dust mite allergen levels in the home: use of the acaricide, pirimiphos methyl. Clin. Allergy 15: 234–240).

Recently, compounds such as benzyl benzoate, paragerm and the like have been used as acaricides (Penaud, A., J. Nourrit, P. Timon-David and J. Charpid. 1977. Results of a controlled trial of the acaricide paragerm on *Dermatophagoides* spp. In dwelling houses. Clin. Allergy 7: 49–53; Schober, G., G. Wetter, E. Bischoff, J. E. M. H. van Bronswijk and F. M. Kniest. 1987. Control of house dust mites(*Pyroglyphidae*) with home disinfectants. Exp. Appl. Acarol. 3: 179–189).

It has been reported that many plant extracts and oils have characteristics of repellence of egg and insecticidal activity for various stored products. It has been reported that oils derived from *Acorus calamus* have insecticidal activity against *Callosobruchus chinensis, Sitophilus oryzae, Sitophilus granaries, Tribolium confusum,* and *Rhizopertha dominica* F (El-Nalhal, A. K. M., Schmidt, G. H., Risha, E. M. 1989. Vapours of *Acorus calamus* oil-a space treatment for stored-product insects. J. Stored Prod. Res., 25:211–216). And also, compounds derived from plants have characteristics of potent insecticidal activity for insecticide-resistant pests (Arnason, J. T., Philogene, B. J. R., Morand, P., Lmrie, K., Lyengar, S., Duval, F., Soucy-Breau, C., Scaiano, J. C., Werstiuk, M. H., Hasspieler, B., downe, A. E. R. 1989. Naturally occurring and synthetic thiophenes as photoactivated insecticides. In Insecticides of Plant Origin, eds. by Arnason, J. T., Philogene, B. J. R., Morand, P. ACS symposium Series 387:164–172). And, Ginkgo biloba leaf extracts have characteristics of potent insecticidal activity against carbofuran, fenobucarb and diazinon-resistant *Nilaparvata lugens* (Ahn, Y. J., Kwon, M., Park, H. M., Han, C. G. 1997. Potent insecticidal activity of *Ginkgo biloba*-derived trilactone terpenes against *Nilaparvata lugens*. In Phytochemical Pest Control Agents, eds. by Hedin, P., Hollingworth, R., Miyamoto, J., Masler, E., Thompson, D., ACS Symposium series 658:90–105).

Most plant extracts and oils having these activities belong mainly to monoterpenes or phenylpropanoids (Coats J, R., karr, L. L., Drewes, C. K. 1991. Toxicity and neurotoxic effects of monoterpenoids in insects and earthworms. In Naturally Occurring Pest Bioregulators, eds. by P. A. Hedin. ACS Symp. Ser. 449:305–16; Konstantopoulou, L., Vassilopoulou, L., Mauragani-Tsipidov, P., Scouras Z. G. 1992. Insecticidal effects of essential oils. A study of the effects of essential oils extracted from eleven Greek aromatic plants on *D. auraria.* Experientia. 48:616–9; Regnault-Roger, C., Hamraoui, A., 1995. Fumigant toxic ativity and reproductive inhibituin induced by monoterpenes on *Acanthosceides obtectus*(Say) (Coleoptera: Bruchidae) a pest of kidney bean(*Phaseolus vulgaris* L.). J. Stored Prod. Res. 31:291–299).These chemical compounds show insecticidal activities against insect species through high volatility. Carvacrol, monoterpenoid isolated from saw dust of *Thujopsis dolabrata,* showed volatile action against agricultural pests and hygienic pests as well as stored-product insects (Ahn, Y. J., Lee, S. b., Lee, H. S., Kim, G. H. 1998. Insecticidal and acaricidal activity of carvacrol and β-thujaplicine derived from *Thujopsis dolabrata* var. *hondai* sawdust. J. Chem. Ecol. 24:81–90).

Control against stored-product insects is mainly dependent on the continuous treatment of liquid agents or fumigants and control of mites has been primarily dependent on chemical acaricides.

Repetitive treatments of these chemical agents have been used for several decades, resulting in generation of resistant species against various types of pesticides and causing adverse effects to environments and humans. Some stored-product insects have developed the resistance for fumigants such as methyl bromide and phosphine, and especially mites of *Pyroglyphidae* species having resistance to both DDT and lindane have been found. So, research has been carried out to find alternatives for these agents. In order to develop natural acaricides much effort has been focused on plant materials used for folk remedies as well as aromatic compounds having pleasant perfume. (Miyazaki, Y., M. Yatagai, and M. Takaoka. 1989. Jpn. J. Biometeor. 26: 105–108; Watanabe, F., S. Tadaki, M. Takaoka, S. Ishino and I. Morimoto. 1989. Killing Activities of the volatiles emitted from essential oils for *Dermatophagoides pteronyssinus, Dermatophagoides farinae* and *Tyrophagus putrescentiae.* Syoyakugaku Zasshi 43: 163–168; Yatagai, M. and S. Morita. 1991. Extractives from Yakusugi bogwood and their termicidal activity and growth regulation effects on plant seeds. Mokuzai Gakkishi J. Japan Wood Res. Soc. 37: 345–351; Morita, S., M. Yatagai and T. Ohira. 1991. Antimite and antifungal activities of the hexane extractives from yakusugi bogwood. Journal of the Japan Wood Research Soc. 37(4): 352–357).

SUMMARY OF THE INVENTION

It is an object of the present invention to provide a composition derived from plants with insecticidal activity against mites or stored-product insects.

For this object, the present invention provides an insecticidal compostion comprising the plants consisting of *Paeonia suffruticosa, Cnidium officinale, Cinnamomum cassia,* cinnamon(the stem bark of *Cinnamomum cassia*), mustard (*Brassica Juncea*) and horseradish(*Cholearia aroracia*) and extracts derived from the above plants.

Wherein, *P. suffruticosa, C. officinale* and *C. cassia* can be methanol crude extracts, and cinnamon, mustard and horseradish can be oils. *C. cassia* provides hexane extract and chloroform extract obtained from its methanol crude extract.

Also, the present invention provides an insecticide comprising compounds isolated from the above plants. trans-cinnamaldehyde (formula 1), cinamyl alcohol (formula 2) and salicylaldehyde (formula 3) were isolated from hexane extract of *C. cassia*. Allyl isothiocyanate (formula 4) and butyl isothiocyanate (formula 5) were isolated from both mustard oil and horseradish oil, and salicylaldehyde of formula 3 was also isolated from cinnamon oil.

[Formula 1]

[Formula 2]

[Formula 3]

$H_2C=CHCH_2—N=C=S$ [Formula 4]

$CH_3(CH_2)_3—N=C=S$ [Formula 5]

In addition, the above compounds can be used as a lead compound in order to develop derivatives having increased insecticidal activity, and thus the derivatives of each compound can be used as an insecticide. The derivatives are novel compounds that are obtained by the addition or deletion of hydroxyl group or other chemical functional groups from the common compounds having special activity in order to improve activities or remove problems associated in low activity.

In the present invention, allyl isothiocyanate and butyl isothiocyanate may be used for a lead compound for developing derivatives having increased insecticidal activity against a variety of pests including stored-product insects by modification of isothiocyanate (R—N=C=S). Also, salicyaldehyde belongs to propanoid compound and is a very simple compound with aldehyde group in the position of ortho of phenol structure, and therefore, its carbon-side chains can be modified to develop new compounds having increased activity.

DETAILED DESCRIPTION OF THE INVENTION

The present invention provides an insecticidal compostion derived from plants. It is preferred that the composition is selected from the group consisting of *Paeonia suffruticosa, Cnidium officinale, Cinnamomum cassia,* mustard (*Brassica juncea*) and horseradish (*Cholearia aroracia*). More preferably, the composition includes at least one selected from the group consisting of methanol extracts from *P. suffruticosa,* methanol extracts from *C. officinale,* methanol extracts from *C. cassia,* cinnamon oil, mustard oil and horseradish oil wherein, cinnamon is the stem bark of *C. cassia*.

The above insecticidal composition is particuraly active against mites, and the present invention measured acaricidal activity against *Dermatophagoides pteronyssinus* and *Dermatophagoides farinae*. In order to isolate acaricidal material from the above plants, methanol extracts were obtained from *P. suffruticosa, C. officinale* and *C. cassia* respectively, and cinnamon oil, mustard oil and horseradish oil were obtained from cinnamon, mustard and horseradish respectively.

In addition, the methanol extract from *C. cassia* is further isolated by using hexane, chloroform, ethyl acetate and butanol. It was confirmed that hexane and chloroform fractions have acaricidal activity. Thus hexane and chloroform fractions can be applied to a composition for controlling mites and to an insecticide.

Also, the present invention provides trans-cinnamaldehyde, cinnamyl alcohol and salicylaldehyde isolated from *C. cassia,* ally isothiocyanate and butyl isothiocyanate isolated from mustard oil and horseradish oil. The trans-cinnamaldehyde is the compound of formula 1, the cinnamyl alcohol is the compound of formula 2, the salicylaldehyde is the compound of formula 3, the allyl isothiocyanate is the compound of formula 4 and butyl isothiocyanate is the compound of formula 5. The mixture containing trans-cinnamaldehyde, cinnamyl alcohol and salicyaldehyde has a synergic effect for controlling mites compared to using of each compound alone, so it is preferable to use a mixture of trans-cinnamaldehyde, cinnamyl alcohol and salicyaldehyde.

Also, in the present invention, strong insecticidal activity of cinnamon oil was confirmed by filter-paper impregnated method method for 3 species of stored-product insects, *Lasioderma serricorne* Fab., *Sitophilus oryzae* L. and *Callosobruchus chinensis* L., and its insecticidal activity was originated from its fumigation activity. It also was confirmed that *C. cassia* and cinnamon, origin of cinnamon oil, have insecticidal effects.

For the insecticidal composition to show effective insecticidal activity, the insecticide may contain the plants or methanol extracts or the above compounds, or may be mixed with material applied to common insecticides. The amount of this composition preferably ranges from about 0.01 to 70%. In particular, cinnamon oil and salicylaldehyde ranges from 5 to 10% and from 2 to 5% by weight respectively. But, the amount of this composition may preferablely vary depending on the type of acaricide and method for sprinkling the acaricide. Types of insecticide against mites can be formulated as a spray, a solution type ointment and a solid type ointment gel, and the insecticide against stored-product insects can be formulated as a fumigant.

The present invention will be explained in more detail with reference to the following Examples. However, the following Examples are to illustrate the present invention and the present invention is not limited to them.

EXAMPLE 1

Preparation of Sample, and Plants and Oils Having Acaricidal Activity

Plants were screened for acaricidal activity and found that *Paeonia suffruticosa, Cnididum officinale, Cinnamomum cassia,* cinnamon, mustard and horseradish have insecticidal activity, especially acaricidal activity.

The Methanol Extracts 300 g of each of *Paeonia suffruticosa, Cnidium officinale,* and *Cinnamomum cassia* was finely powdered using a mixer, and the resultant was blended with 500 ml of methanol for 3 days in a 500 ml Erlenmeyer flask and extracted twice with methanol at room temperature and pooled. The combined filtrate was concentrated in vacuo at 35° C. Cinnamon oil, mustard oil and horseradish oil used in the present invention were obtained from cinnamon, mustard and horseradish using steam distillation.

[Test 1]

Mites for Acaricidal Activity Test

Two kinds of mites were used for the acaricidal activity. American house dust mite (*Dermatophagoides farinae*) and European house dust mite (*Dermatophagoide pteronyssinus*) were maintained at 75±5% RH (relative humidity) at 25±1° C., and were provided a feed mixture of fish meal and multi-vitamins in a ratio of 1 to 1 on a 12.5×10.5×5 cm container.

Test of Acaricidal Activity

The starting concentration is important for the primary screening of bioactive compounds from plant extracts and oils. In the present invention, a concentrations of compounds were set up in specific ratios in a 2 ml microtube with 1 mg of the compounds for several tests, and the mites were observed with a microscope. 1 mg of the methanol extracts or oils were suspended with 40 µl of methanol and were transferred to a colorless microtube (2 ml). The microtube was vertically shaken several times to disperse the contents to the wall and cap of the microtube and it was placed in a freeze dryer for 1 hour in order to volatilize the solvent. Twenty-five mites were placed on the prepared microtube, and all treatment groups were transferred to an incubator kept at 25±1 ml. Active mites only were selected with a fine brush under a microscope. Mortalities were determined with a microscope at 24 hours and 48 hours after treatment. Mites were considered dead if appendages did not move when prodded with a fine brush. All tests were replicated four or more times. The percentage mortality was determined and transformed to arcsine square-root values for analysis of variance (ANOVA). Treatment means were compared and separated by Scheffe's test at the P=0.05 (SAS Institute, 1996). Means (±standard error) of untransformed data are reported. Controls received 40 µl of methanol.

Table 1 shows acaricidal activity of the methanol extracts and oils.

TABLE 1

| | Mortality (Means ± standard error, %) | | | |
| | D. farinae | | D. pteronyssinus | |
| Plant | 24 hr | 48 hr | 24 hr | 48 hr |
| --- | --- | --- | --- | --- |
| *Paeonia suffruticosa* | 98.3 ± 1.7 | 100 | 100 | — |
| *Cinnamomum cassia* | 100 | — | 100 | — |
| *Cnidium officinale* | 88.3 ± 6.0 | 95.0 ± 5.0 | 91.7 ± 4.4 | 98.3 ± 1.7 |
| Cinnamon oil (*C. cassia*) | 100 | — | 100 | — |
| Mustard oil (*B. juncea*) | 97.0 ± 1.3 | 100 | 99.0 ± 1.3 | 100 |
| Horseradish oil (*C. aroracia*) | 99.0 ± 1.3 | 100 | 100 | — |

The acaricidal activity of the above Table 1 were obtained from treatment with 1 mg of the methanol extracts or oils in a 2 ml microtube, and the time is the time elapsed after treatment with the methanol extracts and oils. The tests of Table 1 were replicated five times.

All the methanol extracts and oils except *Cnidium officinale* had a strong acaricidal activity of 100% against two species of house dust mites at 48 hours after treatment. In particular, *Cinnamomum cassia* and cinnamon oil had 100% acaricidal activity against mites at 24 hours after treatment.

EXAMPLE 2

The acaricidal compounds of the methanol extracts from *Cinnamomum cassia* prepared by Example 1 were isolated and purified. 20 g of the methanol extracts were suspended in 800 ml of distilled water and 800 ml of n-hexane. The mixture was transferred to a separatory funnel (2 ml), capped, and after shaking well, it was separated into a water portion and a hexane portion. After 30 min, a first hexane portion was separated using another separatory funnel. The water portion was mixed with 800 ml of hexane and separated to a second hexane portion in the same manner. The remaining water portion was blended with 800 ml of chloroform, capped, and after shaking well, it was separated into a water portion and a chloroform portion. After 30 min, a first chloroform portion was separated. The water portion was mixed with 800 ml of chloroform and separated to a second chloroform portion in the same manner as separating the hexane portion. The remaining water portion was blended with 800 ml of ethyl acetate and separated twice to an ethyl acetate portion in the same manner as separating the hexane portion. The remaining water portion was blended with 800 ml of butanol and separated to a butanol portion in the same way. A hexane portion, a chloroform portion, an ethyl acetate portion, a butanol portion and a water portion were obtained by the above separatory method. The water portion was concentrated in a freeze dryer, and the hexane portion, the chloroform portion, the ethyl acetate portion and the butanol portion were concentrated in an EYELA autojack NAJ-160(Japan).

The mortaltity was determined by performing the test 1 four times over the concentrated portion, and it is shown in Table 2.

TABLE 2

| Portion | Number of treated mites | Mortality (Means ±standard error, %) | | | |
|---|---|---|---|---|---|
| | | D. pteronyssinus | | D. farinae | |
| | | 24 hr | 48 hr | 24 hr | 48 hr |
| Hexane portion | 100 | 100a | 100a | 100a | 100a |
| Chloroform portion | 100 | 100a | 100a | 100a | 100a |
| Ethyl acetate portion | 100 | 2.7 ± 2.7b | 2.7 ± 2.7b | 4.0 ± 2.3b | 5.3 ± 1.3b |
| Butanol portion | 100 | 5.3 ± 1.3b | 6.7 ± 1.3b | 6.7 ± 1.3b | 6.7 ± 1.3b |
| Water portion | 100 | 2.7 ± 1.3b | 4.0 ± 0b | 2.7 ± 2.7b | 4.0 ± 2.3b |
| Control | 100 | 0b | 0b | 0b | 0b |

Mean followed by the same letter in column are not significantly different (P=0.05, Scheffe's test). Mortalities were transformed to arcsine square-root before ANOVA. Means (±standard error) of untransformed data are reported.

According to Table 2, the hexane portion and the chloroform portion have 100% acaricidal activity against two kinds of mites.

EXAMPLE 3

Figure 1:
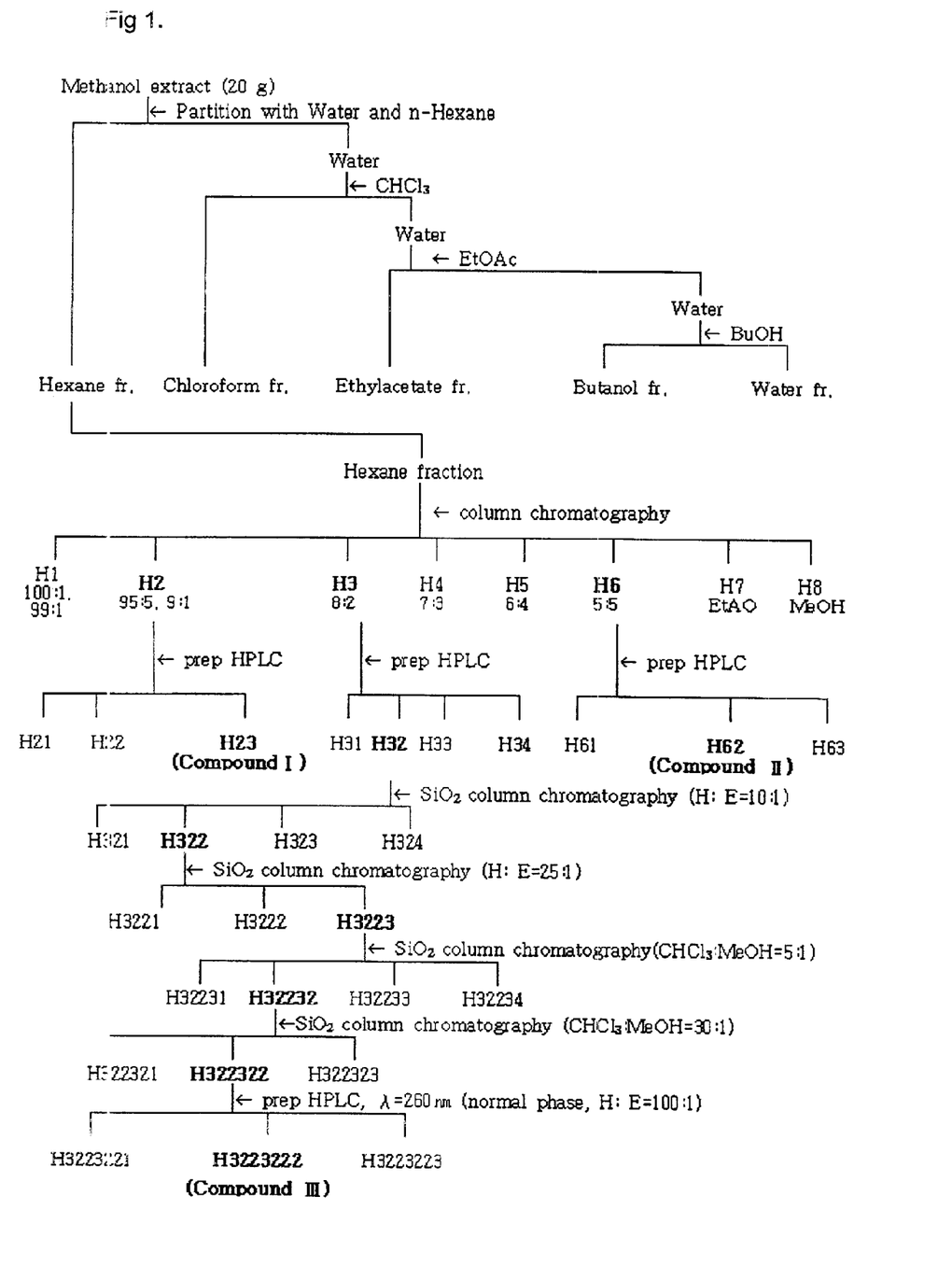
FIG. 1 is a flow chart of the separating steps that isolate the insecticidally effective compounds from the hexane portion of methanol extracts from *Cinnamomum cassia*.

Isolation of an Acaricidal Compound (a) Between the hexane portion and the chloroform portion prepared by Example 2, the acaricidal compounds were isolated from the hexane portion. FIG. 1 shows the procedure that isolates the active compounds of the hexane portion derived from *Cinnamomum cassia* bark.

1st Chromatography

The hexane portion (10 g) was chromatographed on a silica gel column (Merck 70–230 mesh, 600 g, 5.5 i.d.×70 cm), and successively eluted with a stepwise gradient of hexane-ethyl acetate. The ratios of hexane to ethyl acetate used in the stepwise gradient were 100:1, 99:1, 95:5, 90:10, 80:20, 70:30, 60:40, 50:50 and 0:100, and fractions of each ratio were collected as H1, H2, H3, H4, H5, H6, H7 and H8 respectively. The eight fractions were tested as to their mite control efficacies by the acaricidal test of Test 1, and as a result, the three fractions, H2 (40.1% yield), H3 (4.2% yield) and H6 (8.8% yield) that had acaricidal activity were isolated. Each fraction was analyzed by thin layer chromatography (TLC), and fractions with a similar TLC pattern were pooled.

2nd Chromatography

The active fractions isolated from the 1st silica gel chromatography were rechromatographed.

The H2, H3, and H6 fractions were isolated on an high performance liquid chromatography (Spectra System P2000, Thermo Separation Products, USA).

The H2 was eluted with hexane-ethyl acetate (9:1) at a flow rate of 4.0 ml/min. The column was a μ Porasil silica (19×300 mm, Waters) and detected at 260 nm. The three fractions, H21, H22 and H23 were obtained and the H23 fraction was found to be the active fraction, a compound I. The H3 fraction was eluted with hexane-ethyl acetate (8:2) in HPLC. H31, H32, H33 and H34 were obtained and the H32 fraction was found to be active.

The H6 fraction was eluted with hexane-ethyl acetate (7:3) in HPLC. H61, H62 and H63 were obtained and the H62 fraction was found to be a compound II.

3rd Chromatography

The active H32 fraction prepared by the second chromatography was further isolated.

The H32 fraction was eluted with hexane:ethyl acetate (10:1) in silica gel chromatography and the active fraction H322 and the inert fractions H321, H322, H323 and H324 were isolated.

4th Chromatography

The active H322 fraction prepared by the 3rd chromatography was further isolated.

The H322 fraction was eluted with hexane:ethyl acetate (25:1) in silica gel chromatography and the active fraction H3223 and the inert fractions H3221, H3222 were isolated.

5th Chromatography

The active H3223 fraction prepared by the 4 tho chromatography was further isolated.

The H3223 fraction was eluted with chloroform:methanol (5:1) in silica gel chromatography and the active fraction H32232 was isolated.

6th Chromatography

The active H32232 fraction prepared by the 5th chromatography was further isolated.

The H32232 fraction was eluted with chloroform:methanol (30:1) in silica gel chromatography and the active fraction H322322 was isolated.

The H322322 fraction was eluted with hexan:ethyl acetate (100:1) in μ Porasil silica (19×300 mm, Waters) at a flow rate of 4.0 ml/min, absorbance of 260 nm. The Three fractions, H3223221, H3223222, H3223223, were obtained and the H3223223 fraction was found to be a compound III.

Figure 2:
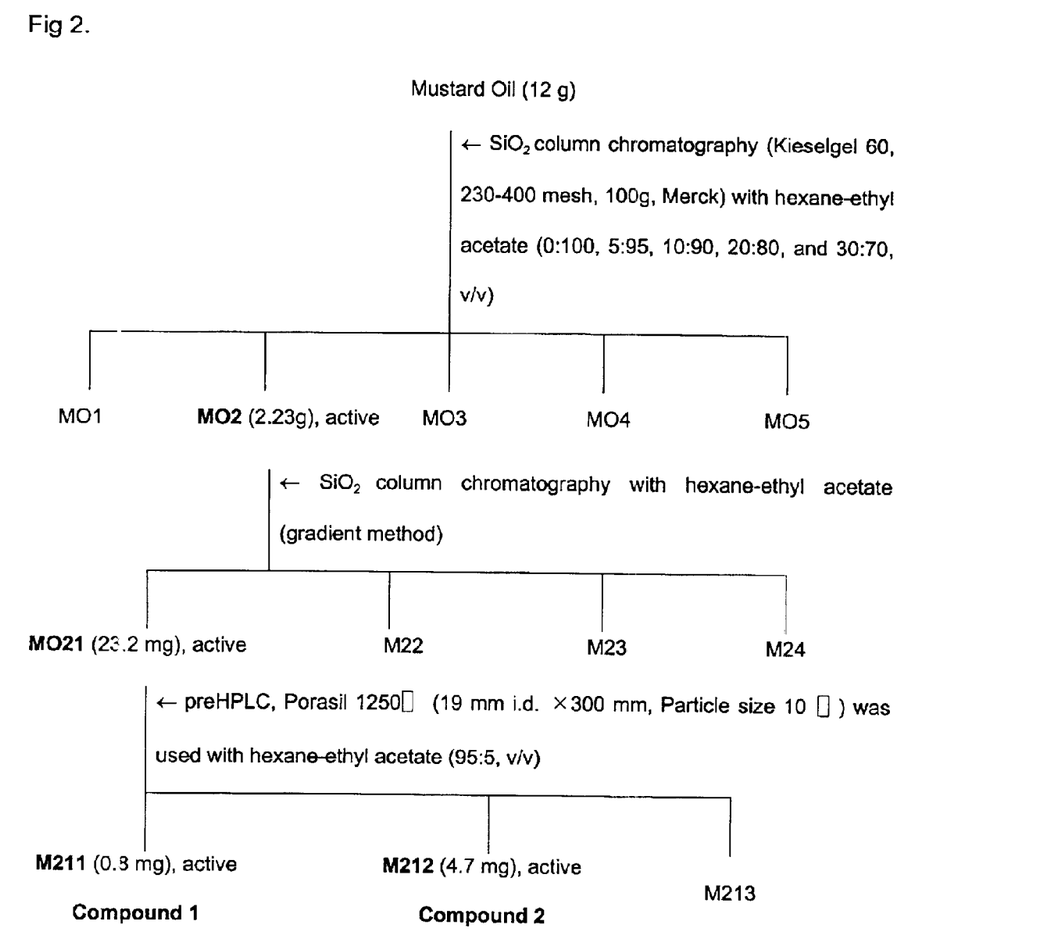
FIG. 2 is a flow chart of the separating steps that isolate the insecticidally effective compounds from mustard oil.

(b) Mustard oil prepared by Example 1 was isolated for searching for the biologically active constituents. FIG. 2 shows the procedure that isolates the active compound of mustard oil.

1 st Chromatography

The mustard oil (12 g) was chromatographed on a silica gel column (Merck 70–230 mesh, 600 9, 5.5 i.d.×70 cm), and successively eluted with a stepwise of hexane-ethyl acetate. The ratios of hexane to ethyl acetate used in the stepwise gradient were 100:0, 95:5, 90:10, 80:20, 70:30, 50:50, 30:70 and 0:100, and fractions of each ratio were collected as MO1, MO2, MO3, MO4 and MO5. The five fractions were tested as to their mite control efficacies by the direct contact test 1, and MO2 (2.23 g) fraction showed an potent acaricidal activity. Column fractions were analyzed by TLC (silica gel G), and fractions with a similar TLC pattern were pooled.

2nd Chromatography

The active fractions isolated from the 1st silica gel chromatography were rechromatographed one more time on a silica gel column using the same method as 1st chromatography. Four fractions were obtained, and MO21 (23.2 mg) fraction produced a potent activity against the house dust mites.

3rd Chromatography

The active fraction, MO21 was further fractionated on a preparatory HPLC for separation of the biologically active constituents. The fraction was eluted with hexane-ethyl acetate (95:5). The column was a μ Porasil silica (19×300 mm, Waters), and was detected at 260 nm. The two fractions, MO211 and MO212 were obtained and both fractions were found to be the active principles compound I and compound II, respectively.

Figure 3:
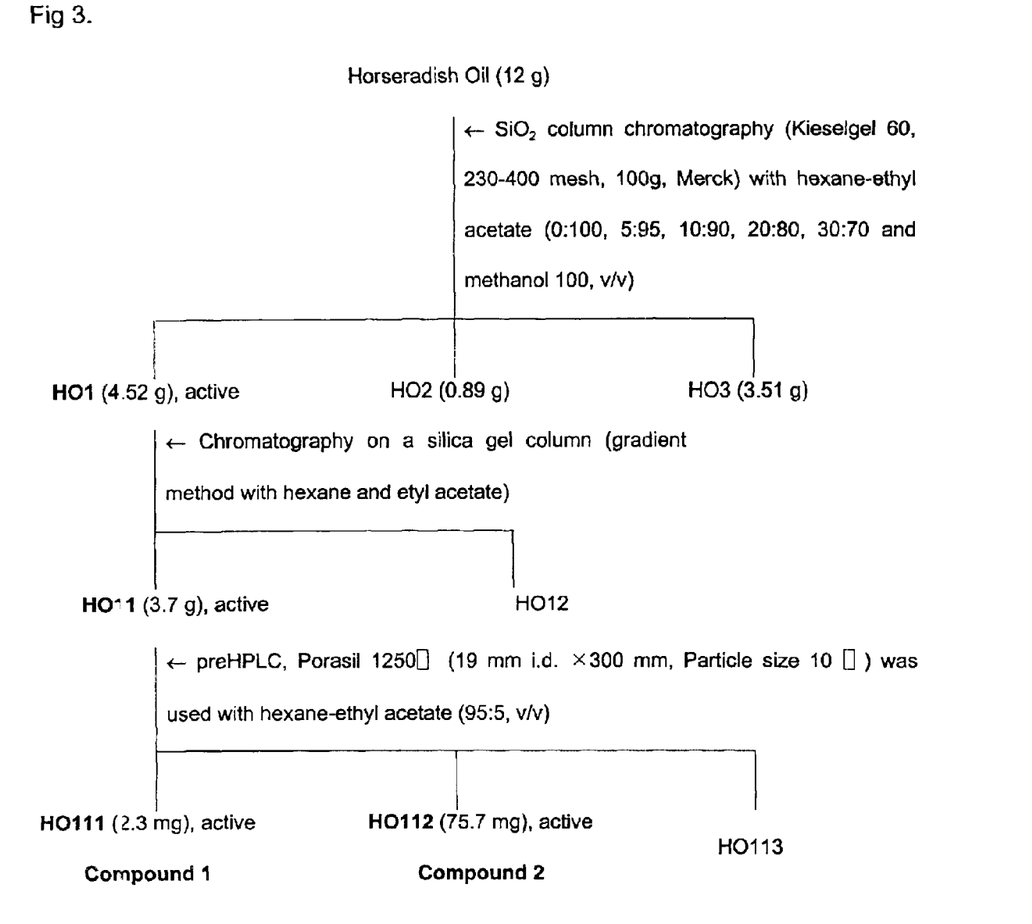
FIG. 3 is a flow chart of the separating steps that isolate the insecticidally effective compounds from horseradish oil.
Figure 4:
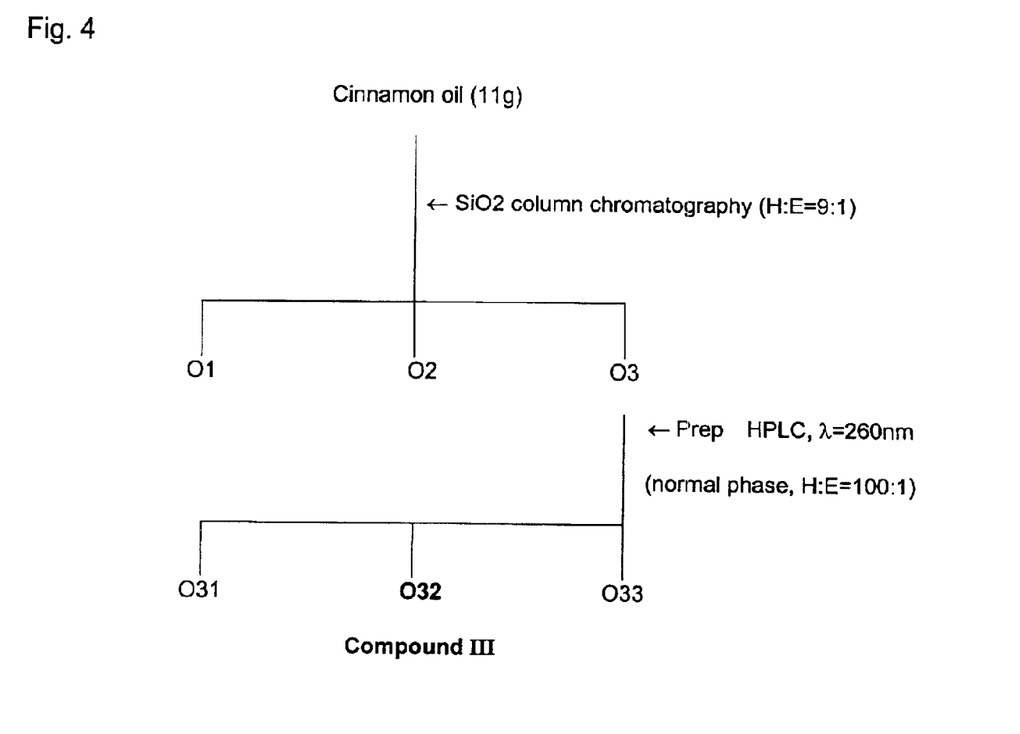
FIG. 4 is a flow chart of the separating steps that isolate the insecticidally effective compounds from cinnamon oil.

(c) Horseradish oil prepared by Example 1 was isolated for searching for the biologically active constituents. FIG. 3 shows the procedure that isolates the active compound of horseradish oil.

1st Chromatography

The horseradish oil (12 g) was chromatographed on a silica gel column, and successively eluted with a stepwise gradient of hexane-ethyl acetate. The ratios of hexane to ethyl acetate used in the stepwise gradient were 100:0, 95:5, 90:10, 80:20, 70:30 and 0:100, and fractions of each ratio were collected as HO1, HO2 and HO3. The five fractions were tested as to their mite control efficacies by the direct contact test 1, and HO1 (4.52 g) fraction showed an potent acaricidal activity. Column fractions were analyzed by TLC, and fractions with a similar TLC pattern were pooled.

2nd Chromatography

The bioactive fraction, HO1 isolated from the 1st silica gel chromatography was successively rechromatographed on a silica gel column, using with hexane/ethyl acetate (95:5, v/v). Two fractions were obtained, and HO11 (3.7 mg) fraction produced a potent activity against the house dust mites.

3rd Chromatography

The active fraction, HO11 was further fractionated on a preparatory HPLC for separation of the biologically active constituents. The fraction was eluted with hexane-ethyl acetate (95:5). The column was a $\mu$ Porasil silica (19×300 mm, Waters) and detected at 260 nm. Among the three fractions, HO111, HO112 and HO113 obtained, HO111 and HO112 showed a strong acaricidal activity. Finally, two acaricidal principles 1 (compound I) and 2 (compound II) were isolated, respectively.

Analysis of the Active Compounds

Structural determination of the active fractions (compound I, compound II, compound III) isolated from Example 3 (a), (b) and (c) was made by spectral analysis. $^1H$ and $^{13}C$ NMR spectra were recorded in deuterochloroform with a Bruker AM-500 spectrometer at 400 and 100 MHz, respectively. EI-MS spectra were obtained on a JEOL JMS-DX 30 spectrometer.

The three active compounds isolated from Example 3 (a) were characterized as trans-cinnamaldehyde, cinnamyl alcohol and salicyl aldehyde.

The two active compounds isolated from Example 3 (b) and (c) were characterized as butyl isothiocyanate and allyl isothiocyanate. Accordingly the active components of the mustard oil and the horseradish oil were the same.

[Test 2] The active compounds of Example 3 were measured using the direct contact application.

Acaricidal Test (a) The acaricidal activity of trans-cinnamaldehyde, cinnamyl alcohol and salicylaldehyde contained in *Cinnamomum cassia* was determined by the direct contact application, and the results are shown in Table 3 and Table 4.

TABLE 3

| | Mortality (Means ±standard error, %) | | | | | |
|---|---|---|---|---|---|---|
| | trans-cinnamaldehyde | | cinnamyl alcohol | | salicylaldehyde | |
| Conc(mg/tube) | 24 hr | 48 hr | 24 hr | 48 hr | 24 hr | 48 hr |
| 1 | 100a | 100a | 99.0 ± 1.0a | 100a | 100a | 100a |
| 0.5 | 84.0 ± 5.2a | 94.0 ± 2.6a | 90.0 ± 2.6a | 97.0 ± 1.9a | 89.0 ± 5.2a | 92.0 ± 1.6a |
| 0.4 | 33.0 ± 2.5b | 42.0 ± 4.2b | 56.0 ± 2.8b | 62.0 ± 2.6b | 44.0 ± 2.8b | 46.0 ± 2.6b |
| 0.3 | 25.0 ± 2.5bc | 32.0 ± 2.8b | 35.0 ± 2.5c | 40.0 ± 3.7b | 22.0 ± 2.6c | 27.0 ± 2.5c |
| 0.25 | 9.0 ± 1.9cd | 10.0 ± 2.6bc | 15.0 ± 1.9d | 14.0 ± 2.6c | 7.0 ± 3.0d | 8.0 ± 2.8d |
| 0.2 | 7.0 ± 1.0cd | 9.0 ± 1.0c | 6.0 ± 1.2d | 10.0 ± 1.2c | 6.0 ± 1.1d | 9.0 ± 1.0d |
| 0.125 | 6.0 ± 3.5d | 9.0 ± 2.5c | 1.0 ± 1.0e | 3.0 ± 1.9d | 0e | 0e |
| Control | 0e | 0d | 0e | 0d | 0e | 0e |

Mean followed by the same letter in column are not significantly different (P=0.05, Scheffe's test). Mortalities were transformed to arcsine square-root before ANOVA. Means (±standard error) of untransformed data are reported.

Table 3 shows acaricidal activity against *D. pteronyssinus* in the acaricidal test at 1.0 mg, and the acaricidal activity of all of active compounds was 100% 48 hours after treatment. At 0.5 mg, after 24 hours trans-cinnamaldehyde had 84.0% acaricidal activity, cinnamyl alcohol had 90.0% acaricidal activity, and salicylaidehyde had 89.0% acaricidal activity. But at 0.4 mg and less, there was no significant acaricidal activity.

TABLE 4

| | Mortality (Means ±standard error, %) | | | | | |
|---|---|---|---|---|---|---|
| | trans-cinnamaldehyde | | cinnamyl alcohol | | salicylaldehyde | |
| Conc(mg/tube) | 24 hr | 48 hr | 24 hr | 48 hr | 24 hr | 48 hr |
| 1 | 99.0 a$^c$ | 100a | 99.0 ± 1.0a | 100a | 100a | 100a |
| 0.5 | 94.0 ± 2.6a | 96.0 ± 2.3a | 90.0 ± 2.6a | 97.0 ± 1.9a | 99.0 ± 1.0a | 100a |
| 0.4 | 41.0 ± 2.5b | 45.0 ± 2.5b | 58.0 ± 2.6b | 65.0 ± 1.9ab | 44.0 ± 2.8b | 48.0 ± 2.8b |
| 0.3 | 32.0 ± 1.6bc | 39.0 ± 2.5bc | 39.0 ± 2.6b | 45.0 ± 1.9b | 27.0 ± 1.9c | 37.0 ± 1.9bc |
| 0.25 | 21.0 ± 2.5cd | 30.0 ± 8.7bc | 10.0 ± 3.8c | 10.0 ± 4.1c | 26.0 ± 2.0c | 34.02.6bc |
| 0.2 | 19.0 ± 2.5cd | 29.0 ± 1.9bc | 7.0 ± 1.0c | 7.0 ± 1.0c | 22.0 ± 1.2c | 28.0 ± 1.6c |

TABLE 4-continued

| | Mortality (Means ±standard error, %) | | | | | |
|---|---|---|---|---|---|---|
| | trans-cinnamaldehyde | | cinnamyl alcohol | | salicylaldehyde | |
| Conc(mg/tube) | 24 hr | 48 hr | 24 hr | 48 hr | 24 hr | 48 hr |
| 0.125 | 18.0 ± 2.6d | 23.0 ± 3.4c | 1.0 ± 1.0d | 2.0 ± 1.2c | 20.0 ± 1.6c | 27.0 ± 3.8c |
| Control | 0e | 0d | 0d | 0d | 0d | 0d |

Mean followed by the same letter in column are not significantly different (P=0.05, Scheffe's test). Mortalities were transformed to arcsine square-root before ANOVA. Means (±standard error) of untransformed data are reported.

Table 4 shows acaricidal activity against *D. farinae*. In the acaricidal test at 1 mg, the acaricidal activity of all the active compounds was 100% 48 hours after treatment. At 0.5 mg, after 24 hours trans-cinnamaldehyde had 94.0% acaricidal activity, cinnamyl alcohol had 90.0% acaricidal activity, and salicylaldehyde had 99.0% acaricidal activity. But at 0.3 mg and less, there was no significant acaricidal activity.

(b) The acaricidal activity of allyl isothiocyanate and butyl isothiocyanate contained in both mustard oil and horseradish oil was determined by the direct contact application, and the results are shown in Table 5 and Table 6, respectively.

TABLE 5

| | Mortality (Means ± standard error, %) | | | |
|---|---|---|---|---|
| | *D. pteronyssinus* | | *D. farinae* | |
| Conc(mg/tube) | 24 hr | 48 hr | 24 hr | 48 hr |
| 1 | 100 a | 100 a | 100 a | 100 a |
| 0.5 | 92.0 ± 2.6 a | 94.0 ± 2.6 a | 90.0 ± 2.6 a | 97.0 ± 1.9 a |
| 0.4 | 33.0 ± 2.5 b | 42.0 ± 4.2 b | 44.0 ± 2.8 b | 46.0 ± 2.6 b |
| 0.3 | 25.0 ± 2.5 bc | 32.0 ± 2.8 b | 22.0 ± 2.6 c | 27.0 ± 2.5 c |
| 0.25 | 9.0 ± 1.9 cd | 10.0 ± 2.6 bc | 7.0 ± 3.0 d | 8.0 ± 2.8 d |
| 0.2 | 7.0 ± 1.0 cd | 9.0 ± 1.0 c | 6.0 ± 1.2 d | 9.0 ± 1.2 d |
| 0.125 | 6.0 ± 3.5 d | 9.0 ± 2.5 c | 1.0 ± 1.0 e | 0 e |
| Control | 0 e | 0 d | 0 e | 0 e |

Mean followed by the same letter in column are not significantly different (P=0.05, Scheffe's test). Mortalities were transformed to arcsine square-root before ANOVA. Means (±standard error) of untransformed data are reported.

Table 5 shows acaricidal activity of allyl isothiocyanate isolated from mustard oil and horseradish oil against *D. pteronyssinus* and *D. farinae* at a different level of concentration. Allyl isothiocyanate at 1 mg/tube caused 100% mortality against 2 mites 48 hours after treatment, and at 0.5 mg, it gave 96% and 94% mortality against *D. pteronyssinus* and *D. farinae* at 48 hours, respectively. But at 0.4 mg and less, there was no significant acaricidal activity.

TABLE 6

| | Mortality (Means ± standard error, %) | | | |
|---|---|---|---|---|
| | *D. pteronyssinus* | | *D. farinae* | |
| Conc(mg/tube) | 24 hr | 48 hr | 24 hr | 48 hr |
| 1 | 99.0 a$^c$ | 100 a | 99.0 ± 1.0 a | 100 a |
| 0.5 | 92.0 ± 2.6 a | 96.0 ± 2.3 a | 84.0 ± 5.2 a | 94.0 ± 2.6 a |
| 0.4 | 39.0 ± 2.5 b | 45.0 ± 2.5 b | 44.0 ± 2.8 b | 48.0 ± 2.8 b |
| 0.3 | 32.0 ± 1.6 bc | 39.0 ± 2.5 bc | 26.0 ± 2.0 c | 34.0 ± 2.6 bc |
| 0.25 | 21.0 ± 2.5 cd | 30.0 ± 8.7 bc | 20.0 ± 1.6 c | 27.0 ± 3.8 c |
| 0.2 | 7.0 ± 1.0 cd | 7.0 ± 1.0 cd | 1.0 ± 1.0 e | 3.0 ± 1.9 d |
| 0.125 | 1.0 ± 1.0 d | 2.0 ± 1.2 d | 1.0 ± 1.0 d | 2.0 ± 1.2 c |
| Control | 0 d | 0 d | 0 d | 0 d |

Mean followed by the same letter in column are not significantly different (P=0.05, Scheffe's test). Mortalities were transformed to arcsine square-root before ANOVA. Means (±standard error) of untransformed data are reported.

Table 6 shows the effect of butyl isothiocyanate on the toxicity of *D. pteronyssinus* and *D. farinae*. Butyl isothiocyanate at 1 mg/tube caused 100% mortality against 2 mites 48 hours after treatment, and at 0.5 mg, it gave 94% and 97% mortality against *D. pteronyssinus* and *D. farinae* at 48 hours, respectively. But at 0.4 mg and less, there was no significant acaricidal activity.

As described above, the acaricidal activity of 5 active compounds was dependent on exposure time as well as dose of used compound. However, no great was observed difference in toxicity among mites.

EXAMPLE 4

In order to confirm the synergic effect for the three kinds of acaricidal compounds prepared by example 3, a concentration that had no acaricidal activity was determined. Up to 0.25 mg, there was no acaricidal activity for the two kinds of house dust mites, thus the synergic effect was measured at 0.25 mg.

A mixture was prepared by blending in a ratio of 1 to 1 with 0.25 mg of each active compound, as follows.

(1) trans-cinnamaldehyde+cinnamyl alcohol
(2) trans-cinnamaldehyde+salicyl aldehyde
(3) salicyl aldehyde.+cinnamyl alcohol
(4) trans-cinnamaldehyde+cinnamyl alcohol+salicyl aldehyde The synergic effect of the mixtures was tested for acaricidal activity against *D. farinae* and *D. pteronyssinus*. Table 7 shows the synergic effects.

TABLE 7

| Mixture | Conc (mg/tube) | D. farinae 24 hr | D. farinae 48 hr | D. pteronyssinus 24 hr | D. pteronyssinus 48 hr |
|---|---|---|---|---|---|
| trans-cinnamaldehyde + cinnamyl alcohol | 0.25 + 0.25 | 91.0 ± 3.4a | 98.0 ± 0a | 83.0 ± 1.0b | 100a |
| trans-cinnamaldehyde + salicyl aldehyde | 0.25 + 0.25 | 95.0 ± 1.9a | 99.0 ± 0a | 93.0 ± 2.5a | 100a |
| salicyl aldehyde. + cinnamyl alcohol | 0.25 + 0.25 | 99.0 ± 1.0a | 100a | 95.0 ± 1.9a | 100a |
| trans-cinnamaldehyde + cinnamyl alcohol + salicyl aldehyde | 0.25 + 0.25 + 0.25 | 100a | ND | 99.2 ± 0.8a | 100a |
| benzyl benzoate | 0.25 | 100a | ND | 88.8 ± 3.9b | ND |
| dibutyl phtalate | 0.25 | 92.0 ± 3.8a | ND | 95.2 ± 1.5a | ND |
| DEET | 0.25 | 96.8 ± 3.2a | ND | 16.8 ± 3.4c | ND |
| Control | | 0b | 0b | 0d | 0b | 0b |

Mean followed by the same letter in column are not significantly different (P=0.05, Scheffe's test). Mortalities were transformed to arcsine square-root before ANOVA. Means (±standard error) of untransformed data are reported. ND means 'not detected'.

At 24 hours, each of the mixtures had a strong acaricidal activity. The mixture (trans-cinnamaldehyde+cinnamyl alcohol+salicyl aldehyde) had the strongest synergic effect against two kinds of mites 24 hours after treatment, but at 48 hours, there was no significant difference when compared to the other mixtures. It was confirmed that all three kinds of acaricidal compounds had synergic effects.

The active compounds were compared to organic synthetic compounds (benzyl benzoate, dibutyl phtalate and DEET) which have a strong acaricidal activity. 0.25 mg each of the organic synthetic compounds were treated on D. farinae and D. pteronyssinus, and 24 hours after treatment benzyl benzoate had 100% and 88.8% mortality, dibutyl phtalate had 92.0% and 95.2% mortality, and DEET had 96.8% and 16.8% mortality against D. farinae and D. pteronyssinus, respectively. Therefore the acaricidal activity of the compounds derived from Cinnamomum cassia compare favorably to that of the synthetic compounds.

EXAMPLE 5

Extraction of Essential Oil

Essential oil from Cinnamomum cassia or cinnamon was extracted by steam evaporation method. 500 g was finely powdered using a mixer, and resultant was put in a flask (2000 ml) and over 60° C. steam was transferred to the flask. The steam then transmits heat to volatile compounds in sample, and volatile compounds are evaporated. These compounds were liquefacted by chill water.

[Test 3]

Stored-product Pests for Insecticidal Activity Test

Stored-product pests used in the present invention were adult Lasioderma serricome Fab., adult Sitophilus oryzae L. and adult Callosobruchus chinensis L., and it was selected insects were not exposed to any insecticide. L. serricorne was bred in a beaker(10 cm diameter, 15 cm height) with wheat bran, S. oryzae was bred in a platic container(20×20× 15 cm) with peanuts, and was bred in a plastic container (26×30×20 cm) with red beans. All insects were maintained at 28±1° C., 55±5% RH(relative humidity) and 16:8 hr(day:night) light condition.

Test of Insecticidal Activity 50 mg of cinnamon oil was dissolved in 100 μl methanol and put on paper(Whatman No.2, 4.25 cm diameter) using a micropipette. Right after treatment, paper was transferred to hood and put in hood for about 2 minutes to completely evaporate solvent, and then, the above paper was put on paper treated with 20 adult pests in petri dish and this dish was covered with a lid. 24 hours after insecticide activity was investigated. To faacilitate handling of adult pests by their reducing activity, L. sericorne was put at −4° C. for 2 minutes, S. oryzae was used without this treatment, and C. chinensis was selected by using sucking tube. Healthy pests used in test were selected right before 6 hours of test. They were maintained at 28±1° C., 50–60% RH and 16:8 hr(day:night) light condition. Pest was considered dead if appendages and body did not move when stimulated with a fine bush. Insecticidal activity test was repeated five times, the percetage mortality was determind and transformed to arcsine square-root values for analysis of variance (ANOVA). Treatment means were compared and separated by Scheffe's test at the P=0.05(SAS institute, 1996).

Table 8 shows insecticidal activity of cinnamon oil against stored-product pests.

TABLE 8

| Conc. (mg/paper) | L. serricorne | S. oryzae | C. chinensis |
|---|---|---|---|
| control | 0 d | 0 c | 2.0 ± 2.0 d |
| 50 | 100 a | 100 a | 100 a |
| 25 | 100 a | 100 a | 100 a |
| 20 | 100 a | 100 a | 100 a |
| 15 | 97.3 ± 3.3 a | 100 a | 100 a |
| 10 | 76.8 ± 3.3 b | 100 a | 100 a |
| 5 | 66.8 ± 3.3 c | 16.0 ± 5.1 b | 78.0 ± 3.7 b |
| 2.5 | 0 d | 0 c | 16.0 ± 4.0 c |

Mean followed by the same letter in column are not significantly different (P=0.05, Scheffe's test). Mortalities were transformed to arcsine square-root before ANOVA. Means (±standard error) of untransformed data are reported.

In the above test, 20 adult pests were put each petri dish and each test was repeated 3 times. As Table 8 shows, cinnamon oil exhibited 100% insecticidal activity against 3 species of stored-product pests at a concentration of more than 20 mg, 100% activity against S. oryzae and C. chinensis at 10 mg concentration, and 100% activity against L. serricorne at more than 15 mg concetration.

[Test 6] Isolation of an Insecticidal Compound

Insecticidal compounds were isolated from cinnamon oil exhibited the insecticidal activity in the above Example 5.

1st Chromatography 11 g of cinnamon oil was chromatographed on a silica gel column(Merck 70-230 mesh, 600 g, 5.5×70 cm) using hexane and ethyl acetate at the ratio of 9:1 (v:v). As a result, fractions were collected as O1, O2 and O3, and O3 fraction exhibited insecticidal activity. O3 fraction was analyzed by thin layer chromatography(TLC) and the fraction comprising one spot, one compound, was determined.

2nd Chromatography

The active fraction isolated from the 1st silica gel chromatography was rechromatographed using high performance liquid chromatography(Spectra System P2000, Thermo Separation Products, USA).

The O3 was eluted with hexane-ethy acetate (100:1) at a flow rate of 4.0 ml/min.

The column was a µPorasil silica (19×300 mm, Waters) and detected at 260 nm. Three fractions, O31, O32 and O33 were obtained and O32 fraction was found to be the active fraction, a compound III.

Analysis of the Active Compound

Structural determination of the active fraction (compound m) isolated from the Example 6 was made by standard comparative analysis with comparision to commercial salicylaldehyde (Sigma Chemical Inc, USA) using HPLC.

[Test 7]

The insecticidal activity of the active compound from Example 6 was measured.

Insecticidal Test

Insecticidal activity of salicylaldehyde against stored-product pests was investigated by the insecticidal test of Test 6. Test was repeated 25 times for adult *S. oryzae,* and 10 times for adult *L. serricorne* and adult *C. chinensis.* 10 adult pests were used for each test. The result was shown in Table 9.

TABLE 9

| Conc. | Mortality (Means ± standard error, %) | | |
|---|---|---|---|
| (mg/paper) | *L. serricorne* | *S. oryzae* | *C. chinensis* |
| 5 | 100 a | 100 a | 100 a |
| 2.5 | 100 a | 100 a | 100 a |
| 1.25 | 100 a | 100 a | 100 a |
| 0.625 | 100 a | 97.0 ± 1.5 a | 100 a |
| 0.3125 | 86.7 ± 3.3 b | 7.0 ± 2.1 b | 97.0 ± 1.5 a |
| 0.15625 | — | — | 68.0 ± 3.9 b |

Mean followed by the same letter in column are not significantly different (P=0.05, Scheffe's test). Mortalities were transformed to arcsine square-root before ANOVA. Means (±standard error) of untransformed data are reported.

As Table 9 shows, salicylaldehyde exhibited 100% insecticidal activity against three species at a concentration of 1.25 mg, 100% activity against adult *L. serricome* and adult *C. chinensis* and 97% activity against adult *S. oryzae* at a concentration of 0.625 mg, and 87% activity against adult *L. serricome* and 97% activity against adult *C. chinensis* at a concentration of 0.3125 mg.

EXAMPLE 7

Test was performed to determine if insecticidal activity of cinnamon oil against is originated by direct contact or by fumigation. 10 mg of cinnamon oil was dissolved in 100 ☐ methanol, put on a paper (4.25 cm diameter) using a micropipette and dried in hood for 120 seconds.

10 adults of *S. oryzae* were put in a diet cup (3.6 cm diameter, 4 cm height), and the entrance of the cup was covered by 60-mesh cloth for inhibition of direct contact of adult pests to compound in paper as well as free penetration of air. This cup was put into a lager plastic container (4.7 cm diameter, 8.4 cm height), paper treated with anethole was placed on the top of diet cup (on the cloth), and the entrance of the container was tightly sealed by a lid (an invention device A) or was covered with 60-mesh cloth for free penetration of air (an invention device B). And also, for pests to freely contact to compound treated in paper, paper was put into a large plastic container (4.7 cm diameter, 8.4 cm height), and the entrance of container without diet cup inside was tightly sealed (an invention device C) or was covered with 60-mesh cloth for free penetration of air (an invention device D). The test was repeated 3 times, and control for each invention device was also tested. 24 hours after treatment the number of dead pests was calculated.

The result of the above test was shown in Table 10.

TABLE 10

| Invention device | Mortality (Means ± standard error, %) |
|---|---|
| A | 100 a |
| B | 10.0 ± 0 c |
| C | 100 a |
| D | 33.3 ± 3.3 b |

Mean followed by the same letter in column are not significantly different (P=0.05, Scheffe's test). Mortalities were transformed to arcsine square-root before ANOVA. Means (±standard error) of untransformed data are reported.

24 hours after treatment 100% insecticidal activity of cinnamon oil was observed in the invention devices A and C characterized by the tight sealing of container entrance. But, the invention devices B and D characterized by free penetration of air did not show significant activity. This result indicates that the insecticidal activity of cinnamon oil against stored-product pests is originated from fumigative toxin, not direct contact.

As described above, *Paeonia suffruticosa, Cnidium officinale, Cinnamomum cassia,* cinnamon (the stem bark of *C. cassia*), mustard (*B. juncea*) and horseradish (*C. aroracia*) have insecticidal activity.

Also, trans-cinnamaldehyde, cinamyl alcohol and salicylaldehyde isolated from *C. cassia* have insecticidal activity and when they are blended, they have a synergic effect. Allyl isothiocyanate and butyl isothiocyanate have insecticidal activity. The above compounds and plant extracts especially have arcaricidal activity against mites and can be provided as a control agent against mites which inhabit dust and carpets in homes.

Salicylaldehyde isolated from cinnamon oil have insecticidal activity. In particular, salicylaldehyde has insecticidal activity against stored-product pests. In addition, it was confirmed that the insecticidal activity of cinnamon oil is originated from fumigative toxin, not direct contact. Accordingly, the cinnamon oil or salicylaldehyde can be used as a controller for stored-product pests in the various closed space including homes, greenhouses, storehouses and food processing plants.

What is claimed is:

1. An insecticide comprising: crude extracts from *Paeonia suffruticosa, Cnidium officinale, Cinnamomum cassia,* mustard (*Brassica juncea*) and horseradish (*Cholearia aroracia*).

2. The insecticide according to claim 1, wherein methanol is used to extract said crude extracts.

3. The insecticide according to claim 1, wherein said crude extracts from *C. cassia, B. juncea,* and *C. aroracia* each comprise an oil.

4. The insecticide according to claim 1, wherein a solvent is used to elute said crude extracts, the solvent comprising hexane and ethyl acetate.

5. The insecticide according to claim 4, wherein the solvent comprises approximately 95% by volume hexane and approximately 5% by volume ethyl acetate.

6. The insecticide according to claim 4, wherein said crude extracts are obtained after a plurality of elutions.

7. The insecticide according to claim 6, wherein volume percentages of hexane and ethyl acetate in each solvent of the plurality of elutions are varied.

8. The insecticide according to claim 1, wherein the insecticide is formed as an aerosol.

9. The insecticide according to claim 1, wherein the insecticide is formed as a paste.

10. The insecticide according to claim 1, wherein the insecticide is formed as a gel.

11. The insecticide according to claim 1, wherein the insecticides is formed as a gas.

12. The insecticide of claim 1, wherein the insecticide eradicates *Dermatopragoides* pternoyssirus and *Dermatophagoides farinae.*

* * * * *

UNITED STATES PATENT AND TRADEMARK OFFICE
CERTIFICATE OF CORRECTION

PATENT NO. : 6,855,348 B2
DATED : February 15, 2005
INVENTOR(S) : Young-Joon Ahn et al.

It is certified that error appears in the above-identified patent and that said Letters Patent is hereby corrected as shown below:

Column 1,
Line 11, after the word "an", delete "an"

Column 2,
Line 24, after the letter "a" in "ativity", insert -- c --

Column 8,
Line 15, after the number "4" delete the extra spaceand after the letters "th" delete the extra letter "o"
Line 39, after the word "stepwise" insert -- gradient --

Column 14,
Line 28, after the letters "fa" delete "a"
Line 37, after the letters "determin" insert -- e --
Line 67, after the letters "conce" insert -- n --

Column 15,
Line 27, delete the letter "m" and insert -- III --

Column 16,
Line 2, delete the boxed symbol and insert -- ul --

Signed and Sealed this

Tenth Day of May, 2005

JON W. DUDAS
*Director of the United States Patent and Trademark Office*